(12) United States Patent
Bae et al.

(10) Patent No.: US 12,000,771 B2
(45) Date of Patent: Jun. 4, 2024

(54) LIGHT IRRADIATION APPARATUS

(71) Applicant: SEOUL VIOSYS CO., LTD., Ansan-si (KR)

(72) Inventors: Hee Ho Bae, Ansan-si (KR); Yeong Min Yoon, Ansan-si (KR); A Young Lee, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 312 days.

(21) Appl. No.: 17/630,142

(22) PCT Filed: Jul. 27, 2020

(86) PCT No.: PCT/KR2020/095094
§ 371 (c)(1),
(2) Date: Feb. 15, 2022

(87) PCT Pub. No.: WO2021/015604
PCT Pub. Date: Jan. 28, 2021

(65) Prior Publication Data
US 2022/0276147 A1 Sep. 1, 2022

Related U.S. Application Data

(60) Provisional application No. 62/878,526, filed on Jul. 25, 2019.

(51) Int. Cl.
*G01N 15/1429* (2024.01)
*G01N 1/30* (2006.01)
(Continued)

(52) U.S. Cl.
CPC ........... *G01N 15/1429* (2013.01); *G01N 1/30* (2013.01); *G01N 15/00* (2013.01);
(Continued)

(58) Field of Classification Search
CPC ...... G01N 15/1429; G01N 1/30; G01N 15/00; G01N 15/1436; G01N 21/01; G01N 21/33;
(Continued)

(56) References Cited

U.S. PATENT DOCUMENTS

| 7,869,033 | B2 * | 1/2011 | Masilamani | ....... G01N 21/6486 356/318 |
| 10,175,159 | B2 * | 1/2019 | Wagner | ............. B01L 3/502761 |

(Continued)

FOREIGN PATENT DOCUMENTS

| JP | 2017-203637 | 11/2017 |
| KR | 10-2019-0008786 | 1/2019 |
| WO | 2011-150023 | 12/2011 |

OTHER PUBLICATIONS

International Search Report dated Oct. 27, 2020 in International Application No. PCT/KR2020/095094 (with English Translation).
(Continued)

*Primary Examiner* — Michelle M Iacoletti
*Assistant Examiner* — Noah J. Haney
(74) *Attorney, Agent, or Firm* — Oblon, McClelland, Maier & Neustadt, L.L.P.

(57) ABSTRACT

A light irradiation device including an injection unit to inject a sample, and a light source to apply light to the sample to identify an abnormal cell in the sample, the light source including a substrate and a light emitter including a light emitting diode, in which the light emitted is to cut a genetic material in the sample into sections of different sizes, and to deform the genetic material to different degrees, such that a determination of an abnormality of the sample is based on the degree of deformation, and an irradiation amount or intensity of the light is at an intensity in which a cytotoxicity value of the sample is greater than or equal to a predetermined value, and a ratio of a degree of deformation of the (Continued)

genetic material of the normal sample to that of the abnormal sample is set to be a minimum value.

20 Claims, 16 Drawing Sheets

(51) Int. Cl.
*G01N 15/00* (2006.01)
*G01N 15/01* (2024.01)
*G01N 15/1434* (2024.01)
*G01N 21/01* (2006.01)
*G01N 21/33* (2006.01)
*G01N 27/447* (2006.01)
*G01N 33/49* (2006.01)
*G01N 21/64* (2006.01)

(52) U.S. Cl.
CPC ......... *G01N 15/1436* (2013.01); *G01N 21/01* (2013.01); *G01N 21/33* (2013.01); *G01N 27/447* (2013.01); *G01N 27/44721* (2013.01); *G01N 33/49* (2013.01); *G01N 33/491* (2013.01); *G01N 15/01* (2024.01); *G01N 2021/0112* (2013.01); *G01N 21/6428* (2013.01); *G01N 21/6486* (2013.01)

(58) Field of Classification Search
CPC ........... G01N 27/447; G01N 27/44721; G01N 33/49; G01N 33/491; G01N 15/01; G01N 21/6428; G01N 21/6486; G01N 2021/0112
USPC .......................................................... 356/39
See application file for complete search history.

(56) References Cited

U.S. PATENT DOCUMENTS

| 11,287,380 | B2* | 3/2022 | Akasaka ............. G01N 15/1434 |
| 2013/0177921 | A1 | 7/2013 | Chastain et al. |
| 2014/0057865 | A1 | 2/2014 | Fantl et al. |
| 2015/0369793 | A1* | 12/2015 | Kimura .............. G01N 15/1429 |
| | | | 435/39 |
| 2016/0152985 | A1 | 6/2016 | D'Andrea et al. |
| 2016/0202170 | A1* | 7/2016 | Yoshida ............. G01N 33/5005 |
| | | | 435/288.7 |
| 2017/0258821 | A1* | 9/2017 | Christofidou-Solomidou ............. |
| | | | A61K 31/365 |
| 2019/0072484 | A1* | 3/2019 | Sogawa ................ G01N 21/359 |
| 2020/0191701 | A1* | 6/2020 | Ye .......................... G01N 15/14 |

OTHER PUBLICATIONS

Written Opinion of the International Searching Authority dated Oct. 27, 2020 in International Application No. PCT/KR2020/095094 (with English Translation).

Extended European Search Report dated Jan. 16, 2023, issued in European Patent Application No. 20844364.8.

N.R. Prasad, et al., Caffeic acid modulates ultraviolet radiation-B induced oxidative damage in human blood lymphocytes, Journal of Photochemistry and Photobiology B: Biology, Jun. 2009, pp. 196-203.

Farivar, UV-Induced DNA Damage Response in Blood Cells as a Potential Method for Cancer Detection, https://open.library.ubc.ca/soa/cIRcle/collections/ubctheses/24/items/1.0378307, Apr. 2019, p. 4-11, 30-35.

* cited by examiner

LIGHT IRRADIATION APPARATUS

CROSS-REFERENCE TO RELATED APPLICATIONS

This application is a National Stage Entry of International Application No. PCT/KR2020/095094, filed on Jul. 27, 2020, and claims priority from and the benefit of U.S. Provisional Application No. 62/878,526 filed Jul. 25, 2019, each of which is hereby incorporated by reference for all purposes as if fully set forth herein.

BACKGROUND

Field

Exemplary embodiments of the invention relate generally to a light irradiation apparatus.

Discussion of the Background

Cancer is a malignant tumor and is a serious disease that occupies the largest proportion of human deaths.

In order to diagnose cancer, symptoms and signs are investigated. After a thorough medical examination, a number of examinations are generally conducted, such as angiography, CT, ultrasound examination, MRI, endoscope, immunological examination, cell examination, and pathological examination, to determine whether cancer has occurred. These number of complicated examinations are typically costly and require a lot of time.

The above information disclosed in this Background section is only for understanding of the background of the inventive concepts, and, therefore, it may contain information that does not constitute prior art.

SUMMARY

Light irradiation apparatuses constructed according to illustrative implementations of the invention are capable of accurately diagnosing cancer in a simple manner that is less time consuming in a cost-effective way.

Additional features of the inventive concepts will be set forth in the description which follows, and in part will be apparent from the description, or may be learned by practice of the inventive concepts.

According to an exemplary embodiment of the present invention, a light irradiation apparatus is a light irradiation apparatus for applying light to a sample to analyze the sample, in which the light cuts a genetic material in the sample into sections of different sizes depending on a normal sample or an abnormal sample and deforms the genetic material to different degrees, and determines whether the sample is normal or abnormal depending on how much the genetic material is deformed, and an irradiation amount or an irradiation intensity of the light is provided at an intensity such that a cytotoxicity value of the sample is greater than or equal to a predetermined value, and a ratio of a degree of deformation of the genetic material of the normal sample to a degree of deformation of the genetic material of the abnormal sample is set to a minimum value outside an error range.

When the light is applied to the sample, the light may be transmitted into the sample to stimulate a photosensitive material in the sample, and thus, provided in a wavelength band in which reactive oxygen species are generated.

The cytotoxicity value may be 75% or more.

The genetic material may be cut into sections having different sizes depending on the irradiation of light.

The light irradiation apparatus may further include: a light irradiation unit configured to apply the light to the sample; and a reaction unit configured to inject a dyeing material into the sample to react the dyeing material with the sample; and an analysis unit configured to analyze the sample.

Light emitted from the light irradiation unit may include at least a portion of light in a blue wavelength band to an ultraviolet wavelength band.

The light may correspond to at least one of light in UVA, UVB, and UVC wavelength bands and the light in the blue wavelength band.

The light irradiation apparatus may further include a pre-processing unit configured to process the sample before providing the sample to the reaction unit.

The sample may be blood.

The sample may be leukocyte, and the pre-processing unit may separate the leukocyte from whole blood.

The irradiation amount of the light may be set within a limit in which cell viability of the normal sample is 75% or more.

The irradiation amount of the light may be about 5 J/cm$^2$ or less, and the light may be irradiated with an irradiation time of about 15 minutes or less.

The light may be irradiated with a quantity of light of about 1.5 mW/cm$^2$ to about 100 mW/cm$^2$.

The light irradiation unit may include at least two light sources having different wavelengths.

The analysis unit may be implemented in a Comet assay.

The analysis unit may include a data providing unit configured to provide a table quantifying a degree of damage of the genetic material according to a length of a tail in an electrophoresis result, a comparison unit configured to compare lengths of tails of a normal cell and an abnormal cell with the length of the tail stored in the data providing unit, and a determination unit configured to determine whether cancer occurs based on the comparison result of the comparison unit.

The data providing unit may have a table corresponding to either a normal or an abnormal state according to the length of the tail.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

FIG. 4A illustrates an exemplary spectrum of light emitted from the LED of the light irradiation apparatus according to exemplary embodiments of the present invention, and FIG. 4B illustrates another exemplary spectrum of light emitted from the LED of the light irradiation apparatus according to exemplary embodiments of the present invention.

FIG. 9A is a graph showing the results of measuring cytotoxicity by irradiating light to cells, FIG. 9B is a graph showing a damage ratio between a genetic material of abnormal cells and a genetic material of normal cells upon light irradiation, FIG. 9C is a graph showing the results of measuring cytotoxicity according to the amount of hydrogen peroxide, and FIG. 9D is a graph showing a damage ratio between a genetic material of abnormal cells and a genetic material of normal cells according to the amount of hydrogen peroxide.

FIG. 11A illustrates the electrophoresis experiment results when no light is applied to the normal sample, FIG. 11B illustrates the electrophoresis experiment results when light is applied to the normal sample, FIG. 11C illustrates the electrophoresis experiment results when no light is applied to the abnormal sample, and FIG. 11D illustrates the electrophoresis experiment results when light is applied to the abnormal sample.

DETAILED DESCRIPTION

Figure 1:
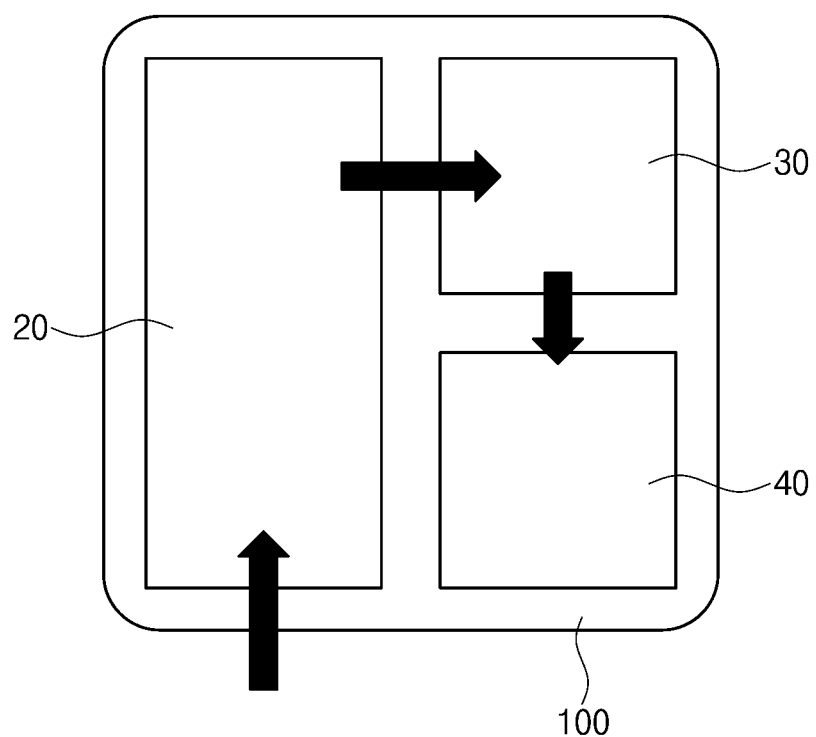
FIG. 1 is a conceptual diagram illustrating a light irradiation apparatus according to an exemplary embodiment of the present invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath"

other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessing units, hard-wired circuits, memory elements, wiring connections, and the like, which may be formed using semiconductor-based fabrication techniques or other manufacturing technologies. In the case of the blocks, units, and/or modules being implemented by microprocessing units or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processing unit (e.g., one or more programmed microprocessing units and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, exemplary embodiments of the present invention will be described in more detail with reference to the accompanying drawings. Exemplary embodiments of the present invention relate to a light irradiation apparatus, and more particularly, to a cancer diagnosis apparatus for diagnosing cancer using a sample.

As used herein, the term "cancer" refers to a "malignant tumor." The tumor refers to a mass of cells that divide abnormally, and may be classified as a benign tumor and a malignant tumor depending on whether it has metastasized to surrounding tissues or other organs. The tumor that may metastasize to surrounding tissues or other organs is referred to as a malignant tumor, and otherwise, is referred to as a benign tumor. Cancer is a disease in which abnormal growth and proliferation of cells that may not be controlled due to the abnormal growth of cells caused by various factors. Abnormally grown and proliferated cells penetrate into surrounding tissues or organs and metastasize.

A "sample" used herein refers to various samples obtained from living organisms. The sample may be used in a diagnostic or monitoring analysis. The sample may be a solid, liquid, or gas collected from a living body. A target from which the sample is collected may include various animals, in particular, a mammal, preferably a primate, more particularly, a human. The sample may include a portion of normal tissue, and may also include cancer tissues, or a portion of tissues suspected of being cancerous. Hereinafter, cells and tissues without cancer, samples including the same, and the like are referred to as normal cells, normal tissues, normal samples, or the like, and cells and tissues with cancer, samples including the same, and the like are referred to as abnormal cells, abnormal tissues, abnormal samples, or the like.

In an exemplary embodiment, the sample may be a liquid sample, for example, blood. The sample may also be in a form of a liquid from which components are separated, for example, blood separated from components, such as leukocyte. However, the inventive concepts are not limited to a particular type or form of the sample, as long as a genetic material can be damaged to different degrees by light emitted from a light irradiation unit, which will be described in more detail later. That is, the sample is sufficient as long as it has a genetic material, such as DNA, RNA, etc.

FIG. 1 is a conceptual diagram illustrating a light irradiation apparatus according to an exemplary embodiment.

Referring to FIG. 1, the light irradiation apparatus 100 includes a light irradiation unit 20 that irradiates light to a sample, a reaction unit 30 that injects a dyeing material into the sample to cause reaction between the dyeing material and the sample, and an analysis unit 40 that analyzes the sample. The sample sequentially moves to the light irradiation unit 20, the reaction unit 30, and the analysis unit 40. The analysis unit 40 may check whether cancer has occurred. The movement path of the sample is indicated by an arrow in FIG. 1.

The light irradiation unit 20 irradiates light to the sample. Light emitted from the light irradiation unit 20 and applied to the sample affects normal samples and abnormal samples differently. For example, light emitted from the light irradiation unit 20 deforms the genetic materials to different levels in the normal samples and the abnormal samples. Details of the light irradiation unit 20 and the light processing will be described later.

Bio-sample to be processed by the light irradiation unit 20 may be provided into the light irradiation apparatus 100 through a sample injection unit. In some exemplary embodiments, the sample may be pre-processed by a pre-processing unit, which may then be provided to the light irradiation unit 20 through the sample injection unit. The pre-processing may include, for example, concentration or separation process on a sample extracted from a human body.

Figure 2:
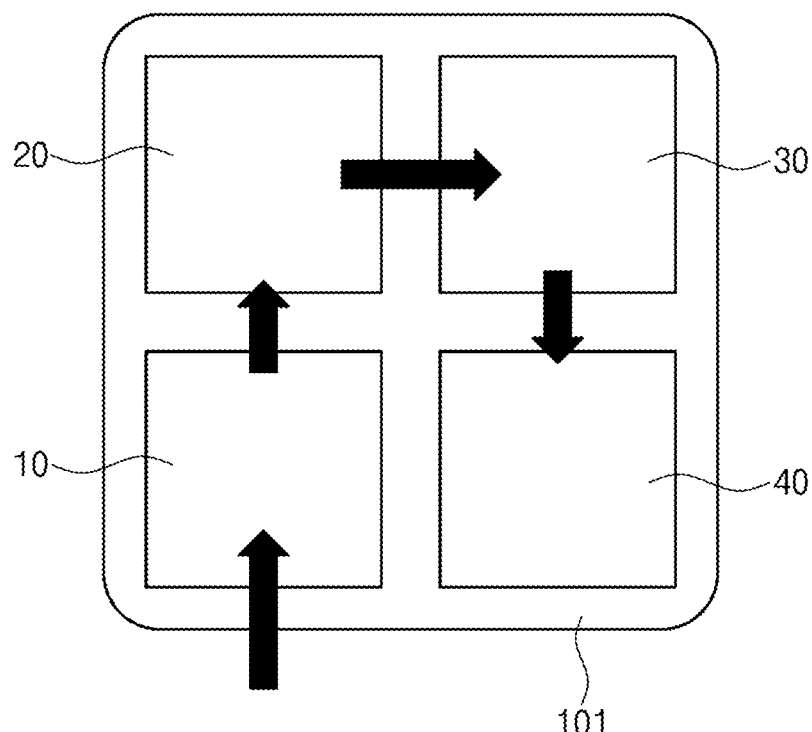
FIG. 2 is a diagram illustrating a light irradiation apparatus according to another exemplary embodiment of the present invention.

FIG. 2 illustrates a light irradiation apparatus according to another exemplary embodiment.

The light irradiation apparatus 101 according to the illustrated exemplary embodiment additionally includes a pre-processing unit 10 that processes a sample provided to the light irradiation unit 20 of FIG. 1.

The pre-processing unit 10 processes the sample in advance, such that the sample may be utilized in the reaction unit 30 and the analysis unit 40. For example, when the sample is blood, the pre-processing unit 10 may separate the blood for each component. More particularly, the pre-processing unit 10 may separate leukocytes from whole blood. When the pre-processing unit 10 is provided, the sample sequentially moves to the pre-processing unit 10, the light irradiation unit 20, the reaction unit 30, and the analysis unit 40. The movement path of the sample is indicated by an arrow in FIG. 2.

The light irradiation unit 20 provides light to the sample. The light irradiation unit 20 according to exemplary embodiments emits light that can affect the genetic material of the sample. Light may include at least a portion of light in a blue wavelength band to an ultraviolet wavelength band. For example, the light irradiation unit 20 may emit light in at least one of UVA, UVB, and blue wavelength bands. As another example, the light irradiation unit 20 may emit light in one of the UVA, UVB, and blue wavelength bands. Alternatively, light in the UVA and UVB wavelength bands, or in the UVB and blue wavelength bands, may be emitted together. Still alternatively, the light in the UVA and blue wavelength bands, or in the UVA, UVB, and blue wavelength bands, may be emitted together.

The light irradiation unit 20 includes at least one or more LEDs to irradiate the above-described light to the sample. The LED may emit light of any one of the UVA, UVB, and blue wavelength bands, and may have a continuous spectrum including at least one of the UVA, UVB, and blue wavelength bands. When the light irradiation unit 20 includes a plurality of LEDs, each LED may be configured to emit only the light in any one of the UVA, UVB, and blue wavelength bands, or may collectively emit mixed light having different wavelengths in at least two wavelength bands.

When light generated from the light irradiation unit 20 is provided to the sample, light reacts with a photosensitizer in a cell to cause cytotoxicity, which may generate reactive oxygen to a certain extent. However, the light irradiation unit 20 according to an exemplary embodiment may emit light in a predetermined intensity and/or strength to minimize the occurrence of cytotoxicity while inducing genotoxicity to the genetic material in the sample. Here, the cytotoxicity refers to cell viability based on a normal sample. In the case of the abnormal samples, even when the same irradiation amount is applied from the light irradiation unit 20, the cell viability may exhibit a smaller value than that of normal cells, and the cell viability may vary depending on the degree of abnormality (that is, progress of cancer). As such, light from the light irradiation unit 20 is set to an intensity and strength that induce damage to abnormal samples while keeping normal samples undamaged as much as possible.

To this end, the irradiation amount of light emitted from the light irradiation unit 20 may be set to be within a limit in which cytotoxicity (that is, cell viability) has at least a predetermined value or more. For example, the irradiation amount of light emitted from the light irradiation unit 20 may be set such that, when the sample is exposed to the light emitted from the light irradiation unit 20, the cell viability is 75% or more based on the normal sample. When cytotoxicity is excessively induced in the sample, both of the normal sample and the abnormal sample may be damaged and kill the cells. In this case, it may be impossible to distinguish between the normal sample and the abnormal sample.

As such, according to exemplary embodiments, the irradiation amount of light emitted from the light irradiation unit 20 needs to be provided to a sample to such an extent that genetic damage (that is, genotoxicity) occurs to a degree that would sufficiently distinguish between the normal sample and the abnormal sample.

In particular, the genetic material in the sample according to exemplary embodiments is cut into sections having different sizes depending on the normal sample or the abnormal sample. Then, the genetic material cut into sections of different sizes are deformed to different degrees to determine whether the sample is normal or abnormal according to the degree of deformation of the genetic material. As such, the intensity and/or the irradiation amount of light is provided to an extent that the cytotoxicity value of the sample is greater than or equal to a predetermined value, while the ratio of the degree of deformation of the genetic material of the normal sample to the degree of deformation of the genetic material of the abnormal sample is sufficiently distinguishable. In general, as the intensity and/or the irradiation amount of light increases, both of the cytotoxicity and genotoxicity may be increased, which may in turn damage the normal sample. As such, according to exemplary embodiments, the ratio of the degree of deformation of the genetic material of the normal sample to the degree of deformation of the genetic material of the abnormal sample may be set to a minimum value outside an error range.

For example, even when the cytotoxicity is about 80%, if the degree of damage to the genetic materials of the normal sample and the abnormal sample may be detected/distinguished by the increased difference in genotoxicity between the normal sample and the abnormal sample, the intensity and/or irradiation amount of light may be set to an extent that the cytotoxicity occurs to about 80%. As another example, even when the cytotoxicity is about 90%, if the degree of damage to the genetic materials of the normal sample and the abnormal sample may be detected/distinguished by the increased difference in genotoxicity between the normal sample and the abnormal sample, the intensity and/or irradiation amount of light may be set to an extent that the cytotoxicity occurs to about 90%.

In exemplary embodiments, in order to satisfy these conditions, light emitted from the light irradiation unit 20 may include at least a portion of light in a wavelength band, which generates reactive oxygen by reacting with a photosensitizer in a cell, for example, light in the blue wavelength band to the ultraviolet wavelength band. In exemplary embodiments, light may correspond to at least one of the light in the UVA, UVB, and UVC wavelengths and the light in the blue wavelength band. For example, light of 365 nm or 405 nm in the blue wavelength band, etc., may also be used.

In exemplary embodiments, light emitted from the light irradiation unit 20 may be irradiated to a sample in a quantity of light of about 1.5 mW/cm$^2$ to about 100 mW/cm$^2$. Here, the irradiation amount of light emitted from the light irradiation unit 20 may be about 5 J/cm$^2$ or less, for example, about 1.4 J/cm$^2$ or less. In this case, light may be irradiated for an irradiation time of about 15 minutes or less. However, the inventive concepts are not limited thereto, and the quantity of light and the irradiation amount may be set differently as long as the above-described cytotoxicity and genotoxicity can be satisfied.

In an exemplary embodiment, light in the UVA wavelength band may be applied to the sample from the light irradiation unit 20 in the quantity of light of 15 mW/cm² for an irradiation time of 1 minute and 30 seconds. In this case, the irradiation amount of light emitted from the light irradiation unit 20 and applied to the sample corresponds to 1.4 J/cm².

In another exemplary embodiment, the irradiation amount of light emitted from the light irradiation unit 20 and applied to the sample is maintained to be about 5 J/cm² or less, for example, about 1.4 J/cm², but the quantity of light emitted from the light irradiation unit 20 may be increased. In another exemplary embodiment, light in the UVA wavelength band may be applied to the sample from the light irradiation unit 20 in the quantity of light of 3 mW/cm² for an irradiation time of 7 minutes and 46 seconds. In another exemplary embodiment, light in the UVA wavelength band may be applied to the sample from the light irradiation unit 20 in the quantity of light of 5 mW/cm² for an irradiation time of 4 minutes and 40 seconds. In another exemplary embodiment, the light in the UVA wavelength band may be applied to the sample from the light irradiation unit 20 in the quantity of light of 10 mW/cm² for an irradiation time of 2 minutes and 20 seconds. In another exemplary embodiment, light in the UVA wavelength band may be applied to the sample from the light irradiation unit 20 in the quantity of light of 50 mW/cm² for an irradiation time of 28 seconds. In another exemplary embodiment, light in the UVA wavelength band may be applied to the sample from the light irradiation unit 20 in the quantity of light of 100 mW/cm² for an irradiation time of 14 seconds.

In exemplary embodiments, when the sample is irradiated with light in the ultraviolet and blue wavelength bands, a genome may be damaged. For example, when a sample is irradiated with light in the UVA or blue wavelength band, light energy may be directly transmitted to the cell of the sample, and the photosensitive material (for example, chromophore or photosensitizer) in the cell is stimulated. The photosensitive material generates reactive oxygen species (ROS) within the cell, and these reactive oxygen species damage the genome. For example, the reactive oxygen species may cut DNA or RNA into multiple irregularly sized sections. In general, in the case of the normal cells, substances such as antioxidant enzymes in vivo serve to protect the normal cells, and prevent the oxidative damage of the genome due to reactive oxygen species, etc. However, in the case of abnormal cells such as cancer cells, the degree of damage to the genome is severer than that in the normal cells. The cancer cells have a high basic level of oxidative stress due to various factors and generate higher reactive oxygen even with the same stimulus. This phenomenon may be further exacerbated as cancer progresses.

According to the exemplary embodiments of the present invention, an LED is used as a light source to apply light to a sample. The LED may apply a predetermined quantity of light to a sample in a much shorter period of time than the existing UV lamp. When an application time of a predetermined quantity of light to a sample is relatively short, more samples may be diagnosed. In addition, when the application time of light is shortened, the stability of the sample may be maintained due to the reduction in the irradiation time. When the sample is not examined as soon as possible after the sample is obtained, the sample is highly likely to be damaged due to various factors. Once the sample is damaged, it is difficult to guarantee the accuracy of the examination. For example, when a sample, such as blood, is to be examined, as the time the sample is exposed to the outside environment increases, the probability that the sample will be damaged by factors other than light, for example, external air, external temperature, or the like, inevitably increases. Therefore, in order to increase the accuracy of the investigation result, it is important to exclude external factors that may damage the sample by minimizing the irradiation time. According to exemplary embodiments, it is possible to examine a sample within a short period of time by using an LED as a light source. In this manner, since the diagnosis may be performed while the stability of the sample is maximized, the diagnostic accuracy may be improved. The difference between the LED and the conventional UV lamp will be described in more later.

In the exemplary embodiments, since the stability of the sample is maximized, additional equipment (for example, a temperature maintenance device for maintaining the environment outside the sample) or the like for securing the stability of the sample may be obviated, and thus, it is possible to simplify cancer diagnosis equipment.

The reaction unit 30 causes a predetermined reaction with a sample to analyze the sample irradiated with light emitted from the light irradiation unit 20. For example, the reaction may be a dyeing reaction, in which the genetic material is dyed to confirm the state of the genetic material.

In exemplary embodiments, the reaction unit 30 causes reaction between the dyeing material and the sample. In this case, the dyeing material used in the reaction unit 30 may vary depending on the type of a dyeing target sample or a genetic material. Examples of the dyeing material may include at least one of Aceto-Carmine, Methylene blue, Wright, Giemsa, a Basic Fuchsin Solution, an Eosin Solution, an orange G solution, a Bismark Brown Solution, a Haematoxylin Solution, Methyl Cellulose, a Safranin Solution, a Congored Solution, a Ringer Solution, an Acid Fuchsin Solution, and a Methyl Green Solution.

The sample reacted with the dyeing material in the reaction unit 30 may emit light in a specific wavelength. Accordingly, a user may easily determine the shape of the dyed sample by detecting the light in the specific wavelength emitted from the reaction unit 30. For example, when the sample to be dyed in the reaction unit 30 is leukocytes, the Giemsa may be used. Since the Giemsa selectively dyes leukocytes, the shape of the sample may be easily determined by observing the wavelength emitted from the dyed leukocytes.

The analysis unit 40 analyzes the sample reacted with the dyeing material.

The analysis unit 40 determines whether the sample is a normal sample or an abnormal sample indicating cancer symptoms. The analysis unit 40 may perform various diagnostic methods to determine whether the sample is the normal sample. In detail, the analysis unit 40 may electrophorese the sample, or detect the quantity of light in the specific wavelength emitted from the sample. For example, the analysis unit 40 may perform a Comet assay to determine whether the sample is the normal sample or the abnormal sample.

The Comet assay is one of the methods for measuring the degree of damage to a genetic material in a cell, for example, DNA, and is a useful research method that may directly measure the degree of damage to DNA in a single cell. In the Comet assay, the sample is sequentially subjected to a process of alkali annealing, alkali dissolution, and alkali sugar precipitation at a high acidity of pH 12.3 or higher, and finally, electrophoresis is conducted. During the electrophoresis, the damaged DNA section in the sample moves toward a specific electrode (for example, an anode) and forms the shape of a comet consisting of a head and a tail. As the damage to DNA increases in cells during the electrophoresis, more DNA sections move from nucleus to a specific electrode, and the length of the tail or the fluorescence intensity becomes proportional to the number of cut DNA helices damaged by light. Intact cells may maintain the original shape of the head without the tail.

The analysis unit 40 may include a data providing unit that provides a table quantifying the degree of damage in the genetic material according to the length of the tail in the electrophoresis result, a comparison unit that compares the length of the tail of the normal cell and the abnormal cell with the length of the tail stored in the data providing unit, and a determination unit that determines whether cancer has occurred based on the result of the comparison unit. The data providing unit may include a table having a value corresponding to one of normality or occurrence of cancer according to the length of the tail.

According to exemplary embodiments of the present invention, it has been described above that, by using an LED as a light source to apply light to the sample, an appropriate amount of irradiation may be applied to the sample in a much shorter period of time as compared to when a conventional UV lamp is used as a light source. In addition, when using an LED as a light source, it is also possible to irradiate only light in a specific wavelength to the cell.

Figure 3:
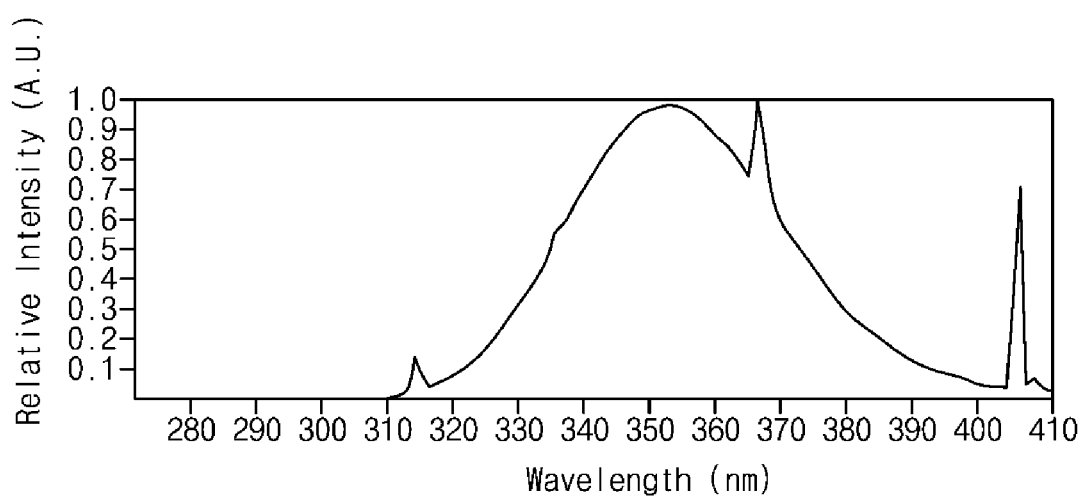
FIG. 3 is a diagram illustrating a spectrum of light emitted from a conventional UV lamp.
Figure 4A:
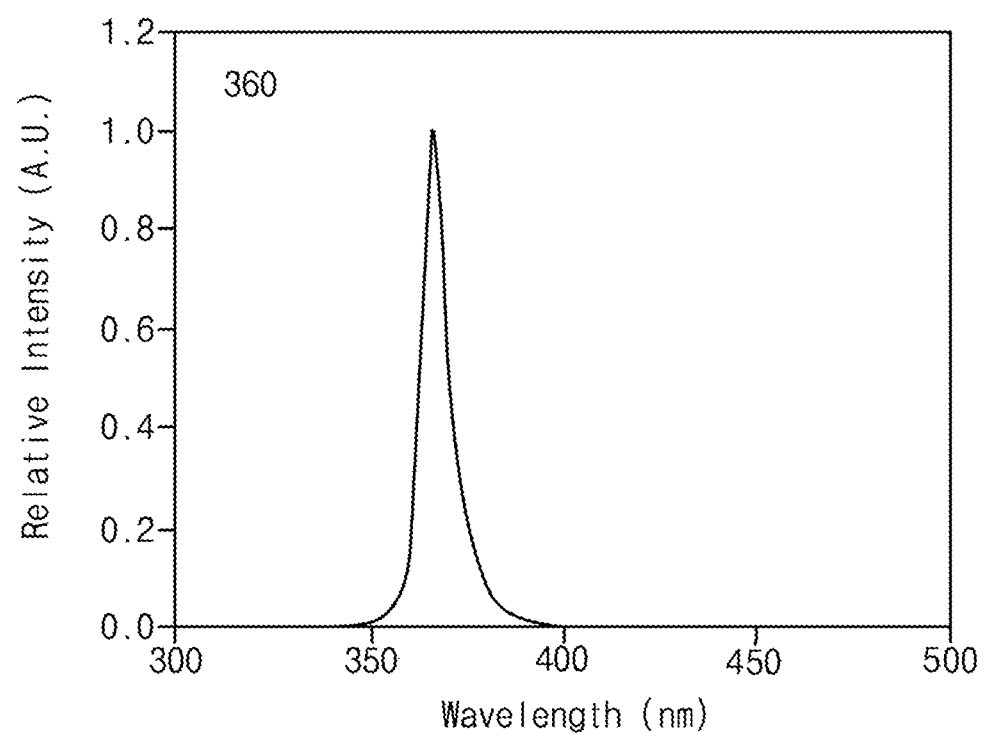
FIGS. 4A and 4B are diagrams illustrating a spectrum of light emitted from an LED in the light irradiation apparatus according to an exemplary embodiment of the present invention. More specifically.
Figure 4B:
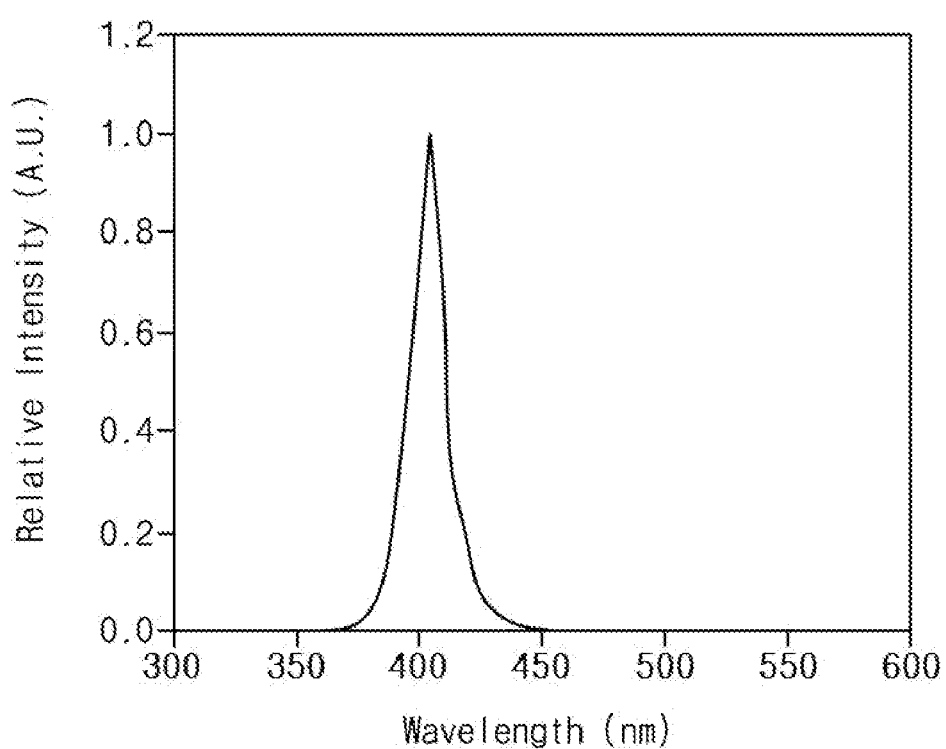

FIG. 3 illustrates the spectrum of light emitted from the conventional UV lamp, and FIGS. 4A and 4B illustrate the spectrum of light emitted from the LED in the light irradiation apparatus according to exemplary embodiments of the present invention. FIG. 4A illustrates an exemplary spectrum of light emitted from the LED of the light irradiation apparatus according to an exemplary embodiment, and FIG. 4B illustrates another exemplary spectrum of light emitted from the LED of the light irradiation apparatus according to an exemplary embodiment.

Referring to FIGS. 3, 4A, and 4B, light emitted from the conventional UV lamp has a broad spectrum compared to light emitted from the LED. Accordingly, in the case of the conventional UV lamp, it is not easy to separate only light in some of the wavelength bands from the emitted light. On the other hand, light emitted from the LED has a sharp peak at a specific wavelength and provides light of a specific wavelength with a very narrow half maximum (FWHM) compared to light from the conventional UV lamp. Accordingly, light of a specific wavelength may be easily selected, and thus, it is possible to provide only the light in the selected specific wavelength to the sample.

More specifically, the conventional UV lamp emits light in a wavelength band of about 320 nm to about 410 nm, and has a peak at about 351 nm.

On the other hand, in the case of the LED according to exemplary embodiments, light of a wavelength band with a narrow half maximum (FWHM) having a peak of about 365 nm as illustrated in FIG. 4A, and a peak of about 405 nm may be selectively used as illustrated in FIG. 4B. Accordingly, unnecessary light in a wavelength band that is not required to be provided to a sample may not be provided to the sample, and light in a wavelength harmful to other parts of a cell unrelated to a genetic material may also not be provided to the sample.

Light having peaks of 365 nm and about 405 nm with a narrow half maximum (FWHM) used in exemplary embodiments may easily damage the genome of the abnormal cells. Light having a peak of 365 nm corresponds to an absorption wavelength of a plurality of photosensitive materials present in the sample cell, and generates reactive oxygen species to induce damage to the genome, especially DNA. Light having a peak of 365 nm stimulates porphyrin, one of the main photosensitive materials in the sample cell, to generate reactive oxygen species, thereby inducing damage to the genome, particularly DNA.

In addition, in the case of a conventional UV lamp, although light is provided to a sample, it may be difficult to accurately limit the quantity of light. However, in the case of the LED, the quantity of light may be precisely limited and provided. For example, the conventional UV lamp may provide light with the quantity of light of about 0.20 mW/cm$^2$ to about 1.20 mW/cm$^2$, but the LED may provide a precise amount in a range of about 1.5 mW/cm$^2$±10%, 15 mW/cm$^2$±10%, and the like.

As described above, it may be difficult to accurately limit the quantity of light in a conventional UV lamp, and thus, the irradiation time may need to be set in a wide range. However, the LED according to exemplary embodiments may provide the required light to the sample within a precise time in a relatively short period of time. For example, the conventional UV lamp needs to irradiate light for about 10 minutes to about 30 minutes, while the LED may precisely adjust the time, such as 1.5 minutes or 15 minutes, according to the quantity of light.

As described above, it is difficult to clearly determine the quantity of light irradiation in a conventional UV lamp due to a relatively wide range of wavelengths, a wide range of quantity of light, and a wide range of irradiation time. On the other hand, the LED according to exemplary embodiments may provide a precise quantity of light irradiation due to a relatively narrow range of wavelength, a narrow range of quantity of light, and a narrow range of irradiation time. For example, when light is provided in the above-described degree, the amount of light irradiation is about 0.1 to about 2.2 J/cm$^2$ in the case of the conventional UV lamp, while is 1.4 J/cm$^2$±10% in the case of the LED.

Moreover, in the case of the conventional UV lamp, a heat dissipation structure for effectively dissipating the generated heat is insufficient, and thus, there is a problem in that heat is transferred to the sample side. When the sample is subjected to heat, the surface of the sample is dried and cause damage to the cell tissue, etc., thereby lowering the accuracy of the normal/abnormal analysis. On the other hand, in the case of the LED, forming the heat dissipation structure is relative easy by utilizing a substrate or the like, and thus, it is possible to effectively prevent heat from being transmitted to the sample side. As a result, the light irradiation apparatus according to exemplary embodiments of the present invention may maintain an environment that would prevent the damage to the sample by obviating factors that may damage the sample as much as possible.

In addition, in the case of the conventional UV lamp, it took a considerable amount of time to reach the maximum quantity of light after turning on a power supply. For example, a PUVA lamp from Philips Lighting Company or the like takes about a minute to reach its maximum light level after turning on a power supply. This means that additional time is required for light irradiation after preparing a sample for diagnosis. However, the longer the time the sample is exposed to the outside after the sample is collected, the greater the sample may be damaged by external factors, such as air, temperature, or the like.

On the other hand, when the LED is used as an ultraviolet light source, the LED reaches the maximum quantity of light immediately after turning on the power supply, with substantially no warm-up time. Accordingly, the LED light source may provide the irradiation amount required for diagnosing normal and abnormal samples in a short time, and minimize the irradiation time. As a result, the possibility that the sample may be damaged by being exposed to the outside is minimized, and thus, the accuracy of sample diagnosis is improved.

As described above, the light irradiation apparatus according to exemplary embodiments of the present invention may easily distinguish a normal person from a cancer patient by using a difference in damage to genome present in a body fluid (blood, etc.). In the case of the conventional cancer diagnosis method, there was a problem that the procedure was complicated and a lot of time and money were required. This is because, in the past, expensive imaging equipment (CT, MRI, or the like) was used to diagnose cancer, or cancer biomarkers using antigen/antibody were used. However, when the light irradiation apparatus according to exemplary embodiments is used, it is possible to simply and accurately diagnose cancer within a short period of time by simply providing a sample containing a genetic material.

The cancer diagnosis method using the above-described light irradiation apparatus may be performed in the following order.

Figure 5:
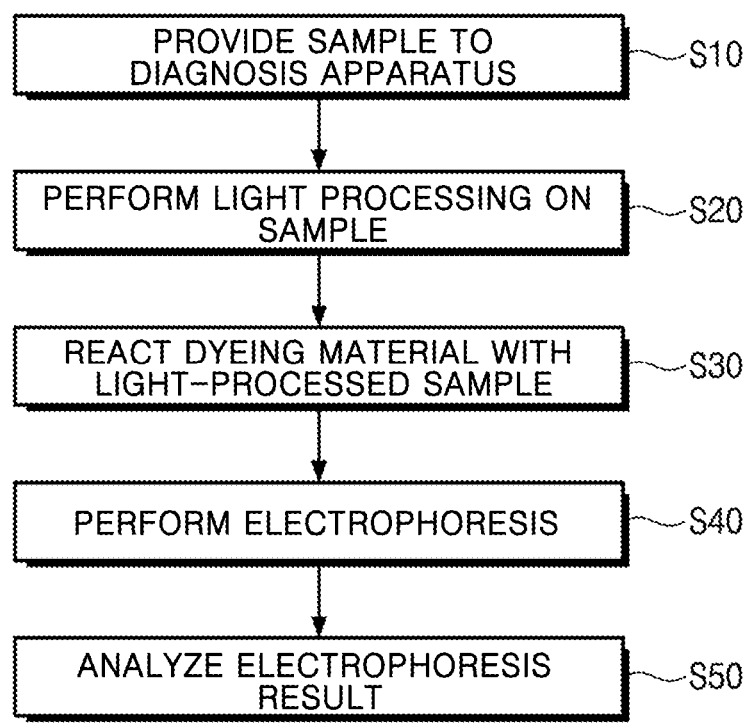
FIG. 5 is a flowchart illustrating a cancer diagnosis method according to an exemplary embodiment of the present invention.

FIG. 5 is a flowchart illustrating a cancer diagnosis method according to an exemplary embodiment of the present invention.

Referring to FIG. 5, the cancer diagnosis method according to an exemplary embodiment of the present invention may include providing a sample to a light irradiation apparatus according to an exemplary embodiment of the present invention (S10), performing light processing on the sample using an LED (S20), reacting a dyeing material with the light-processed sample (S30), performing electrophoresis (S40), and analyzing the electrophoresis result (S50).

First, the sample is provided to the light irradiation apparatus (S10). The sample may be provided into the light irradiation apparatus through a sample inlet. The sample may be selected to contain the genetic material. In an exemplary embodiment of the present invention, the sample may be whole blood, serum, and plasma, for example, leukocytes separated from whole blood. When the light irradiation apparatus includes a pre-processing unit, the sample may be provided in the form of the whole blood. The pre-processing unit may separate the whole blood for each component, in particular, separate leukocytes from whole blood. Then, the pre-processed sample is provided with a light irradiation unit.

Next, the light processing (S20) is performed on the sample. The light processing may be performed by irradiating light in an ultraviolet and/or blue wavelength band to the sample. In an exemplary embodiment of the present invention, light may be irradiated to the sample in the quantity of light of about 1.5 mW/cm$^2$ to about 100 mW/cm$^2$ for light processing. Here, the irradiation amount of the light emitted from the light irradiation unit may be about 1.4 J/cm$^2$ or less, and may be irradiated with an irradiation time of about 15 minutes or less.

Next, the light-processed sample and the dyeing material are reacted (S40). The dyeing material may be bonded to the genetic material to dye the genetic material with a specific color. Since the genetic material to which the dyeing material is bonded exhibits a specific color, light in a specific wavelength band may be emitted from the genetic material. In using a diagnostic kit, by detecting the specific wavelength emitted from the dyed genetic material, the shape of the genetic material after the electrophoresis may be easily confirmed. The reaction with the dyeing material may be performed under the conditions by which the genetic material is not additionally damaged. Specifically, the reaction with the dyeing material may be performed under the neutral condition and temperature condition in which DNA bonding is not damaged.

After the dye and the sample reaction, the sample moves to the analysis unit for analysis (S50). The analysis of the sample may be performed by the electrophoresis.

Specifically, the sample may be provided on a medium pad having electrodes connected to both ends for gel electrophoresis. When performing the electrophoresis, the sample may be provided at a plurality of points and the electrophoresis may be simultaneously performed. Accordingly, the samples provided at the plurality of points may be independently electrophoresed.

Next, the electrophoresis results are analyzed. After the electrophoresis, the sample may have a shape having a head and a tail. The sample shape analysis may involve analyzing the shape of the head and the shape of the tail indicated by the sample after the electrophoresis. In this case, when the electrophoresis is simultaneously performed on samples provided at a plurality of points, the shape of the samples electrophoresed at each point may be detected and averaged. In this manner, the same sample may be analyzed several times at the same time, and thus, the reliability of the sample analysis may be increased.

Figure 6A:
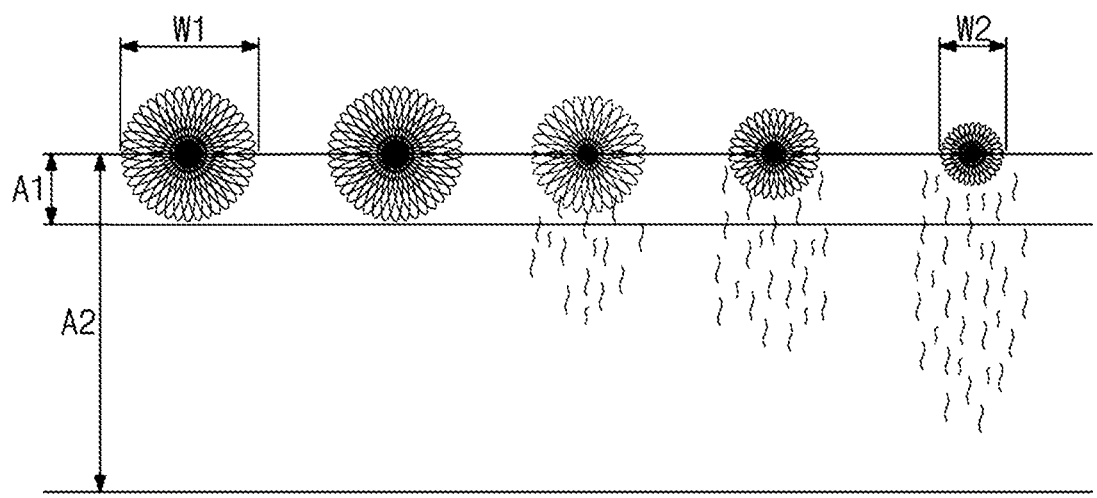
FIG. 6A is a conceptual diagram illustrating shapes of a head and a tail after electrophoresis in normal cells and abnormal cells.
Figure 6B:
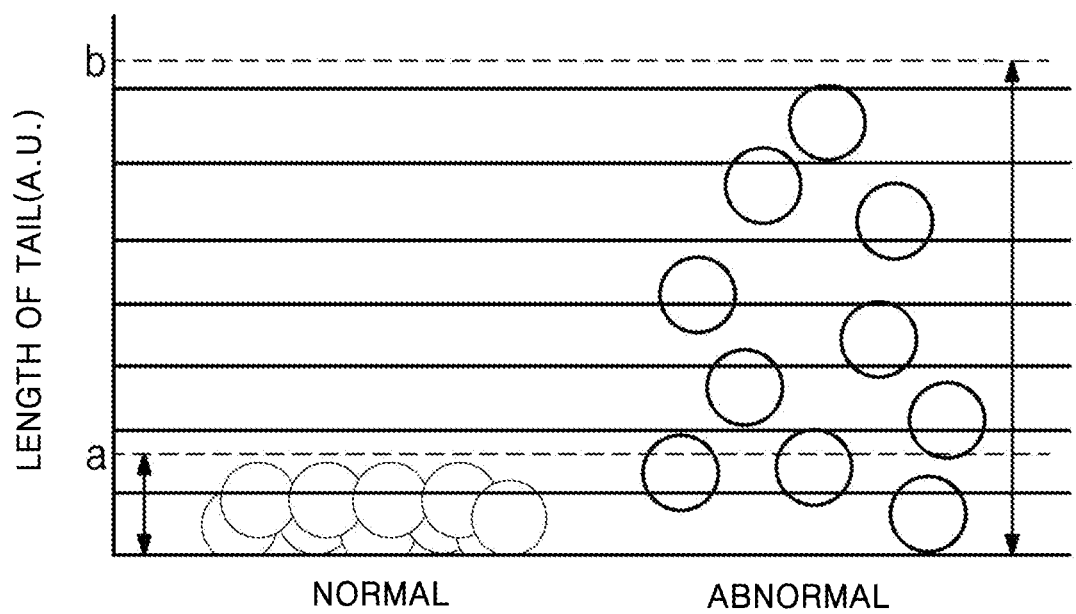
FIG. 6B is a graph showing a distribution of lengths of tails of normal and abnormal samples when the electrophoresis is performed.

FIG. 6A is a diagram conceptually illustrating a shape of a head and a shape of a tail after electrophoresis in normal cells and abnormal cells, and FIG. 6B is a graph showing a distribution of lengths of tails of normal and abnormal samples when the electrophoresis is performed.

Referring to FIG. 6A, a normal cell has a predetermined width and has no tail. However, in the case of an abnormal cell, that is, a cancer cell, has a width smaller than that of the normal cell and has a shape including a tail. For example, assuming that the normal cell has a first width W1 and the abnormal cell has a second width W2, the second width W2 of the abnormal cell has a value less than the first width W1.

This is because, unlike the normal cell, in the case of the cancer cell, a genetic material in the normal cell, for example, DNA, is very easily damaged by light emitted from a light irradiation unit, resulting in a DNA section. More particularly, when normal cells and cancer cells are irradiated with the above-described light (especially UVA or blue light), energy is transmitted into the cells. The energy of the transmitted light stimulates a photosensitive material (chromophore or photosensitizer) in a cell to generate reactive oxygen species (ROS). The reactive oxygen species cause damage in the form of cutting phosphodiester bonding in a genetic material (that is, DNA, RNA, or the like) in a cell. In general, in the case of the normal cell, substances such as antioxidant enzymes in vivo serve to protect the genetic material, thereby preventing oxidative damage through the cutting of the phosphodiester bonding. However, the cancer cell has higher levels of basal oxidative stress than the normal cell due to various factors, thereby generating higher reactive oxygen species even with the same stimuli. Accordingly, more sections with the cut phosphodiester bonding in the genetic material are generated. This DNA section moves toward a specific electrode (for example, anode) during the electrophoresis process and forms the shape of a comet tail. As the DNA damage increases, more DNA moves from a nucleus to a specific electrode. As such, a fluorescence intensity and length of the tail portion may also be increased. The width of the head or the length of the tail may vary to various degrees as illustrated in FIG. 6B, according to the degree of progression from the occurrence of the cancer. On the other hand, in the case of the normal cell, since there is little or no DNA damage, the original nuclear shape without a tail is maintained, or even if a tail appears, the tail would be very short.

In an exemplary embodiment of the present invention, whether a sample is abnormal may be determined according to the length of the tail. For example, the distance from the head to the end of the tail is measured, and when the distance is within a predetermined range, a sample may be determined to be normal, and when the distance is outside the predetermined range, a sample may be determined to be abnormal. As illustrated in FIG. 6A, when the end of the tail from the head is within range A1, a sample may be determined to be normal, and when the end of the tail is within range A2 except for the range A1, a sample may be determined to be abnormal.

Additionally, in an exemplary embodiment of the present invention, when the end of the tail is within the range A2 except for the range A1, but is close to the range A1, it is of course also possible to make a retention determination or an additional review determination for re-inspection.

Referring to FIG. 6B, in the case of the normal sample, the length of the tail is arranged within a predetermined range, whereas, in the case of the abnormal sample, the length of the tail is relatively longer than that of the normal sample, and the distribution also varies compared to that of the normal sample. In an exemplary embodiment of the present invention, whether a sample is abnormal may be determined according to the length and distribution of the tail. That is, when the length of the tail from the head is within a range smaller than 'a', a sample may be determined to be normal, and when the length of the tail varies within a range greater than 'a' and less than 'b', a sample may be determined to be abnormal. Here, 'b' is a value greater than 'a'. The 'b' value may be set to a value greater than the length of the longest tail measured.

In an exemplary embodiment of the present invention, a sample may be determined to be normal or abnormal using the width of the head or the length of the tail during the analysis using the electrophoresis, but a sample may also be determined to be normal or abnormal by measuring the fluorescence intensity.

In an exemplary embodiment of the present invention, when the fluorescence intensity in the electrophoresis result is within a predetermined range, a sample may be determined to be normal, and when the fluorescence intensity is outside the predetermined range, a sample may be determined to be abnormal.

Figure 7:
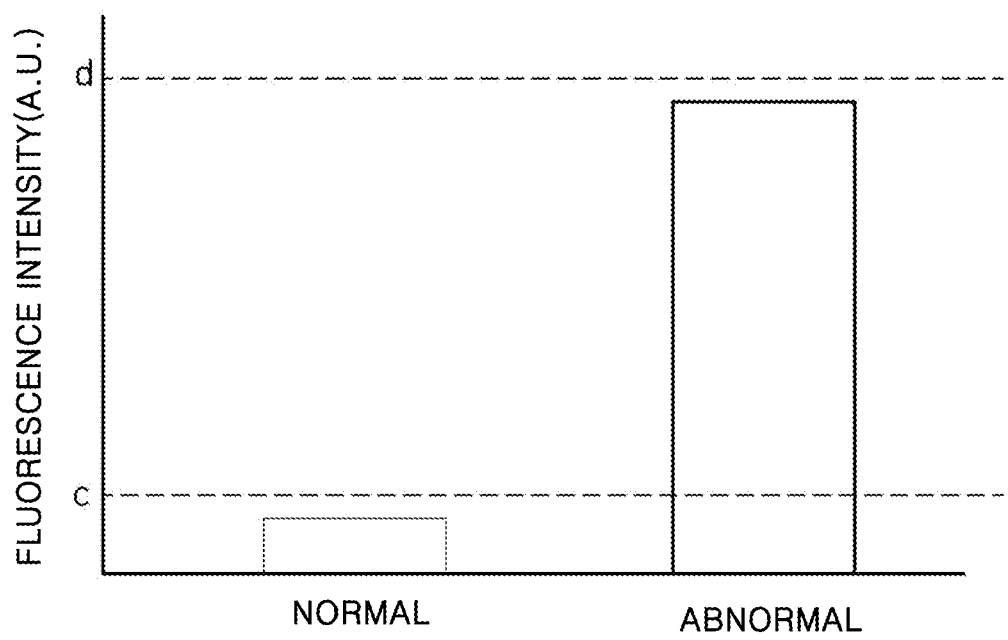
FIG. 7 is a graph showing fluorescence intensities of normal and abnormal samples when the electrophoresis is performed.

FIG. 7 is a graph conceptually illustrating fluorescence intensities of the normal and abnormal samples when the electrophoresis was performed.

Referring to FIG. 7, in the case of the normal and abnormal samples, a difference in fluorescence intensity appears during the electrophoresis.

Since the fluorescence intensity is proportional to the number of cut DNA helices, the fluorescence intensity of the abnormal cells is greatly increased than that of the normal cells. In an exemplary embodiment of the present invention, in consideration of the fluorescence intensity in the normal and abnormal cells, when the fluorescence intensity is within a range smaller than 'c', a sample is determined to be normal, and when the fluorescence intensity is outside 'c' and within a range smaller than 'd', a sample is determined to be abnormal. Here, 'd' is a value greater than 'c'. The 'd' value may be set to a value greater than the largest fluorescence intensity measured.

The range A1 and the range A2, and each value for 'a' and 'b', and 'c' and 'd' may be determined in advance. Before inspecting the sample, the inspection is performed at least once, preferably multiple times, using a cell previously determined to be a normal cell and an abnormal cell as a sample, such that information such as the normal range and the abnormal range and the degree of damage to the genetic material may be determined in advance. The upper limit or lower limit for determining the normality and the abnormality may be provided as a table that quantifies the presence or absence of normality/abnormality according to the width of the head and/or the length of the tail in the electrophoresis result, and the degree of damage to the genetic material.

Figure 8:
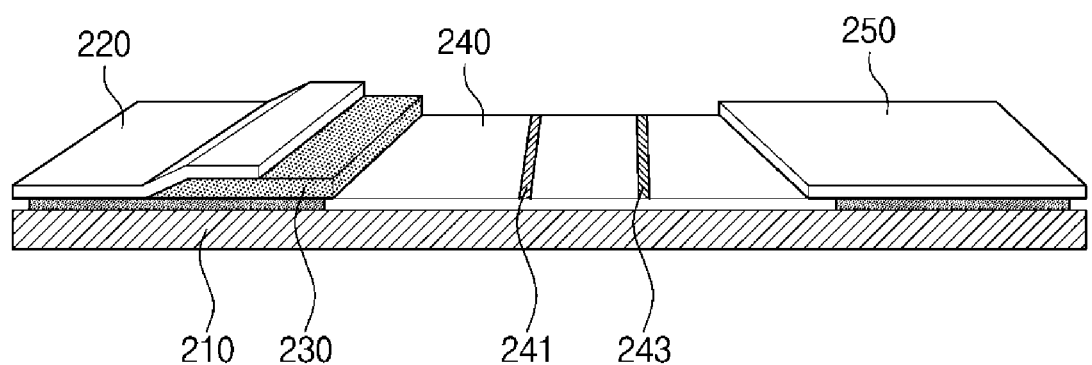
FIG. 8 is a schematic view of a light irradiation apparatus according to an exemplary embodiment of the present invention.

The analysis unit may compare the electrophoresis result of the sample with the information from the table, and finally determine whether cancer has occurred based on the comparison result. The light irradiation apparatus according to an exemplary embodiment of the present invention may be implemented in various forms. FIG. 8 illustrates a light irradiation apparatus according to an exemplary embodiment of the present invention, and illustrates that the reaction unit and the analysis unit are implemented in the form of a strip sensor.

Referring to FIG. 8, a cancer diagnostic strip according to an exemplary embodiment of the present invention is a diagnostic device that enables visual confirmation by detecting the presence or absence of a specific antigen using antigen-antibody reaction of a genetic material present in a sample.

The diagnostic strip according to an exemplary embodiment of the present invention includes a sample injection unit 220 into which a sample is injected, a conjugate unit 230 to which a color expression material is added, a diagnostic unit 240 that performs a detection while a sample is developed, and an absorption unit 250 that promotes the development of the sample. The sample injection unit 220, the conjugate unit 230, the diagnostic unit 240, and the absorption unit 250 are disposed on a support 210.

The support 210 is provided in the form of a bar elongated in one direction. The sample injection unit 220, the conjugate unit 230, the diagnostic unit 240, and the absorption unit 250 are sequentially disposed on the support 210 along one direction.

The sample injection unit 220 is a part into which a sample used for cancer diagnosis is injected, and the sample may be a liquid sample containing a genetic material, for example, blood, or a sample after being irradiated with light. The sample irradiated with light is a sample in which the degree of deformation of the genetic material is different depending on whether the sample is normal or abnormal.

The conjugate unit 230 may include a fluid conjugate of an antibody-labeling particle capable of being specifically bonded to the genetic material contained in the sample. Therefore, as the sample introduced through the sample injection unit 220 passes through the conjugate unit 230, the specific bonding between the genetic material and the fluid conjugate included in the sample occurs. Here, the labeling particle may be provided in various forms, but a phosphor may be used as an example.

The diagnostic unit 240 may be provided as a membrane pad having a porous structure. The diagnostic unit 240 includes a detection area and a control area spaced apart from each other by a predetermined distance. The detection area is for confirming whether a substance to be analyzed (for example, genetic material such as damaged DNA fragments) is present in a sample, and the control area is for confirming whether the sample has passed through the detection area normally. A test line is provided in the detection area of the diagnostic unit 240, and a substance capable of specifically binding an antibody-labeling particle to an antigen-antibody may be provided to the test line. Accordingly, when there is the genetic material to be analyzed in the detection area, whether the genetic material is present may be confirmed by checking the labeling particle of the detection line 241, for example, by checking the presence of fluorescence. When the sample has passed through the detection area and properly arrives at the control area, a control line 243 appears in the control area.

The absorption unit 250 is provided with porosity to absorb the sample. The absorption unit 250 absorbs the sample so that the sample injected through the sample injection unit 220 is developed in the direction of the absorption unit 250 through the diagnostic unit 240. The absorption unit 250 helps a capillary flow in one direction of the sample by absorbing the sample.

According to an exemplary embodiment of the present invention, when a cancer diagnostic strip is used, the cancer diagnosis may be easily performed by detecting the presence or absence of a specific antigen using the antigen-antibody reaction of the genetic material present in the sample. Since the cancer diagnostic strip may be manufactured to be small in size, it is also possible to reduce the size of the overall diagnostic device.

EXPERIMENTAL EXAMPLE

Setting conditions for quantity of light inducing cytotoxicity and genotoxicity

First, a cell was irradiated with light to measure cytotoxicity according to the quantity of light, and cytotoxicity as a positive control was also measured using hydrogen peroxide for cytotoxicity comparison.

Next, a cell was irradiated with light to measure genotoxicity according to the quantity of light, and genotoxicity as a positive control was also measured using hydrogen peroxide for genotoxicity comparison.

Figure 9A:
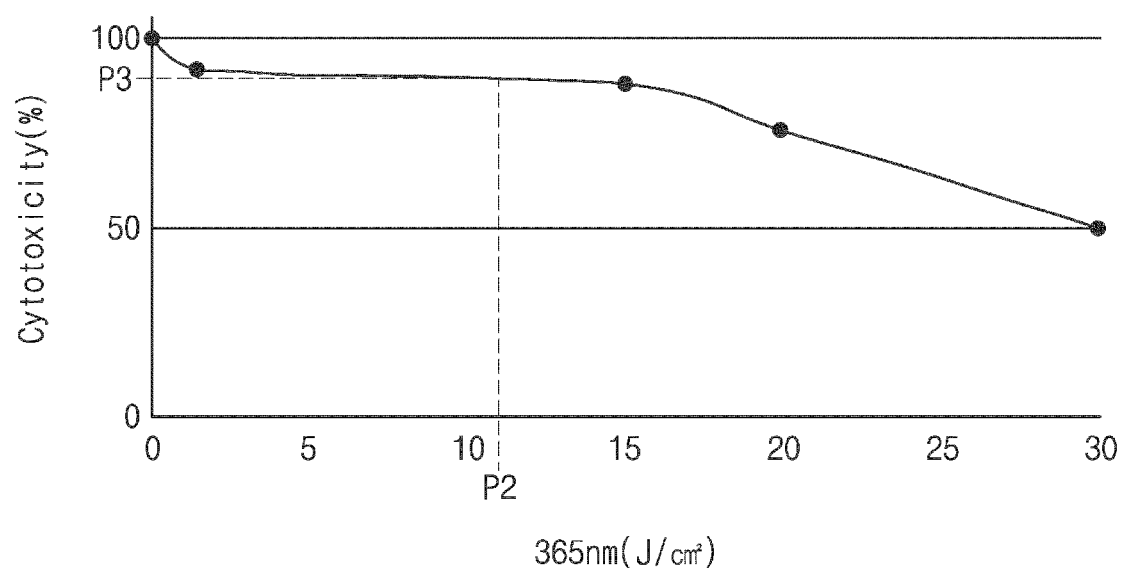
FIGS. 9A and 9B are graphs showing the results of measuring cytotoxicity and genotoxicity by irradiating light to cells.
Figure 9B:
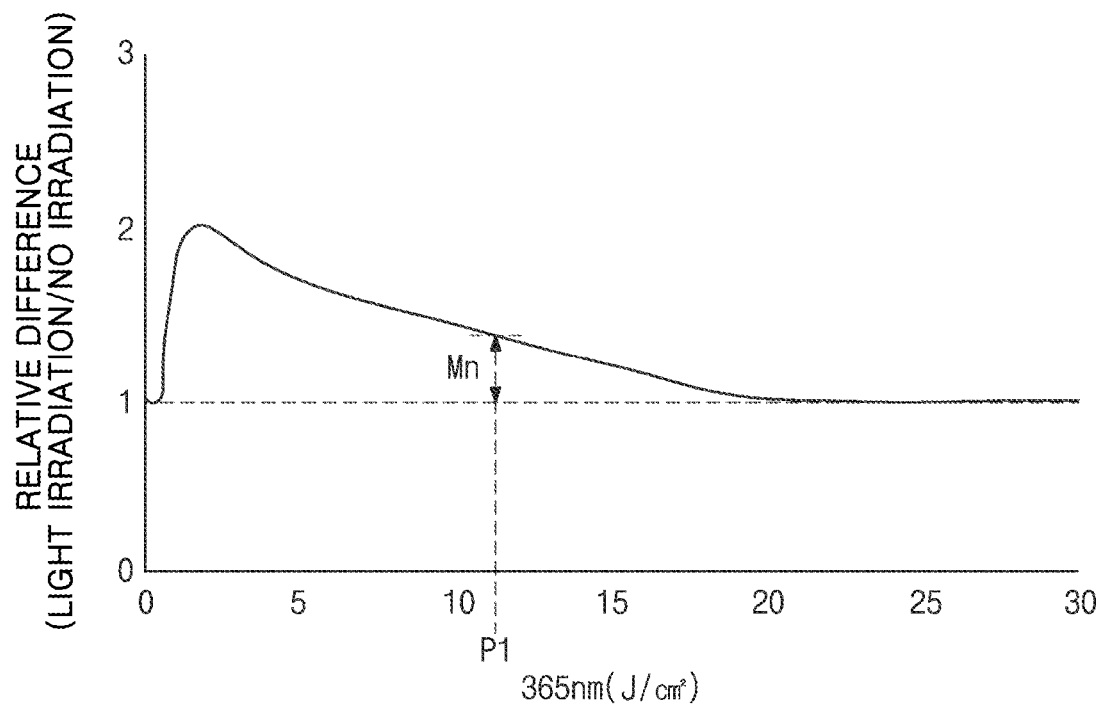
Figure 9C:
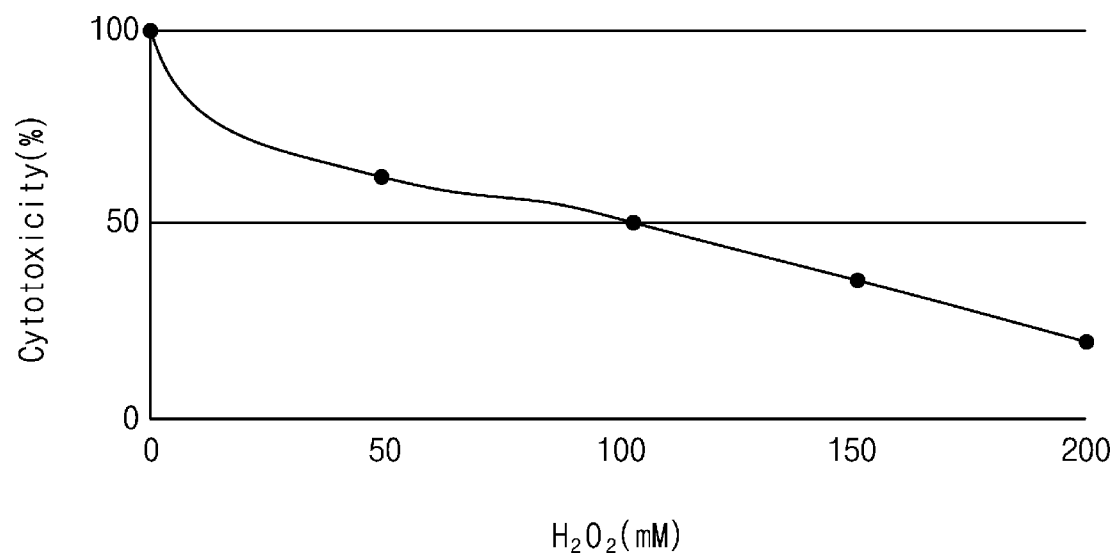
FIGS. 9C and 9D are graphs showing the results of measuring cytotoxicity and genotoxicity according to the amount of hydrogen peroxide. More specifically.
Figure 9D:
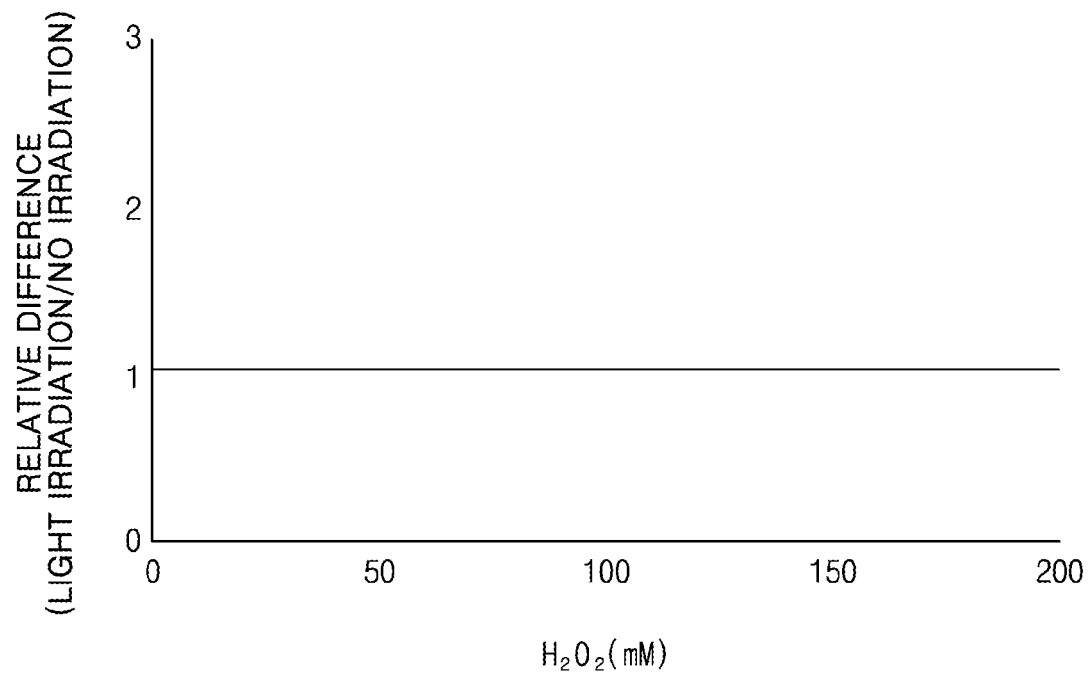

FIGS. 9A and 9B are graphs showing the results of measuring cytotoxicity and genotoxicity by irradiating light to cells, and FIGS. 9C and 9D are graphs showing the results of measuring cytotoxicity and genotoxicity according to the amount of hydrogen peroxide. Here, the graphs of FIGS. 9A and 9C show the cytotoxicity according to the quantity of light energy and hydrogen peroxide, respectively, and FIGS. 9B and 9D illustrate a damage ratio between a genetic material (DNA) of an abnormal cell and a genetic material (DNA) of a normal cell.

Cells used for cytotoxicity and genotoxicity experiments were all peripheral blood mononuclear cells (PBMCs), and light of a wavelength of 365 nm was used using UVA LED.

Referring to FIG. 9A, as a result of measuring cytotoxicity by irradiating light to the cells, the cytotoxicity decreases as the quantity of light energy irradiated to the cells increases, which means that the cell viability gradually decreases with respect to the normal sample. However, the cytotoxicity itself does not decrease linearly with respect to the quantity of light energy, and as illustrated in FIG. 9A, but decreases with a relatively high slope, for example, at the beginning of light irradiation, decreases with a gentle slope, and then decreases with a relatively high slope again.

Referring to FIG. 9B, as a result of measuring the genotoxicity by irradiating light to a cell, it can be confirmed that when the quantity of light energy irradiated to the cell increases, the damage to the genetic material of the abnormal cell occurs more than the damage to the genetic material of the normal cell in the initial stage of applying light. As such, the damage ratio to the abnormal/normal cell rapidly increases, and when the damage ratio exceeds a predetermined value, the degree of damage to the abnormal/normal cells gradually decreases, and eventually, the damage ratio to both the abnormal/normal cells increases and the damage ratio converges to 1.

Here, among the light conditions for distinguishing the abnormal/normal cells, the cells needs to be alive to the extent that the minimum damage ratio may be exhibited to distinguish the abnormal/normal cells. As such, it is important to appropriately set the light quantity conditions of the cell. For example, the quantity of light P1 corresponding to the minimum damage ratio (Mn in FIG. 9B) that may distinguish abnormal/normal cells is set, and in the cytotoxicity, the cytotoxicity value at a position corresponding to the quantity of light P2 may set a lower value P3 as a limit value. Here, the lower limit of the cytotoxicity may be about 75%.

FIGS. 9C and 9D confirm cytotoxicity of a chemical with a positive control, and can be utilized to easily establish conditions for the abnormal cell. In the case of chemically inducing the cytotoxicity, referring to FIG. 9C, the cytotoxicity appears almost linearly according to the amount of hydrogen peroxide. Referring to FIG. 9D, the genotoxicity appears the same regardless of the abnormal/normal cells. Therefore, it is difficult to distinguish the normal/abnormal cells by simply damaging the normal/abnormal cells.

As described above, according to an exemplary embodiment of the present invention, it is possible to set the light quantity condition for inducing the genotoxicity without inducing the cytotoxicity as much as possible.

2. Determination of Normal/Abnormal Samples Using Comet Experiment Method

After setting the amount of irradiated light by the above method, a comet experiment was performed.

The cells used in the experiment were peripheral blood mononuclear cells (PBMCs), and light with a wavelength of 365 nm was irradiated at 1.5 J/cm$^2$ using a UVA LED.

The experiment was performed in the following procedure.

First, the PBMCs were dyed with trypan blue and counted to adjust the cell population ($1 \times 10^5$/ml). In this case, RPMI1640 (10% FBS) was used as a culture medium.

1) When the positive control is $H_2O_2$, PBMCs adjusted to the same cell population were treated at 4° C. for 20 minutes. A vehicle is treated in the remaining groups except for the positive control.

2) After mixing 50 μL cell ($1 \times 10^5$/ml) and 450 μL 37° C. LMAgarose, the mixture was put 75 μL on each slide and incubated at 4° C. for 1 hour.

3) After performing UV treatment at room temperature, the slide was immersed in a pre-chilled lysis solution and maintained at 4° C. overnight.

4) An alkaline unwinding solution (pH>13) was treated at room temperature for 20 minutes.

5) The slide was electrophoresed at 4° C. and 21 V for 23 minutes, washed twice in deionized water for 5 minutes each, and then treated in ethanol of 70% for 5 minutes.

Here, steps 3) to 5) should be performed in a dark room.

6) The slide was dried completely, and treated with 100 μL SYBR® Gold (1:10000/in 10 mM Tris-HCl, pH 7.5, 1 mM EDTA) for 30 minutes in the dark room for observation under a fluorescence microscope.

7) After simply performing the washing, the slide was completely dried again, treated with Anti-fade Mounting Medium (VECTASHIELD, H-1000), and a cover glass is put and then observed with the fluorescence microscope (496 nm/522 nm).

8) After photographing at least 150 cells with the fluorescence microscope, the results were compared by averaging each test group using the results through the analysis program (Comet Assay IV).

9) % tail DNA and olive tail moment (OTM) indicated by the DNA damage were analyzed.

Figure 10:
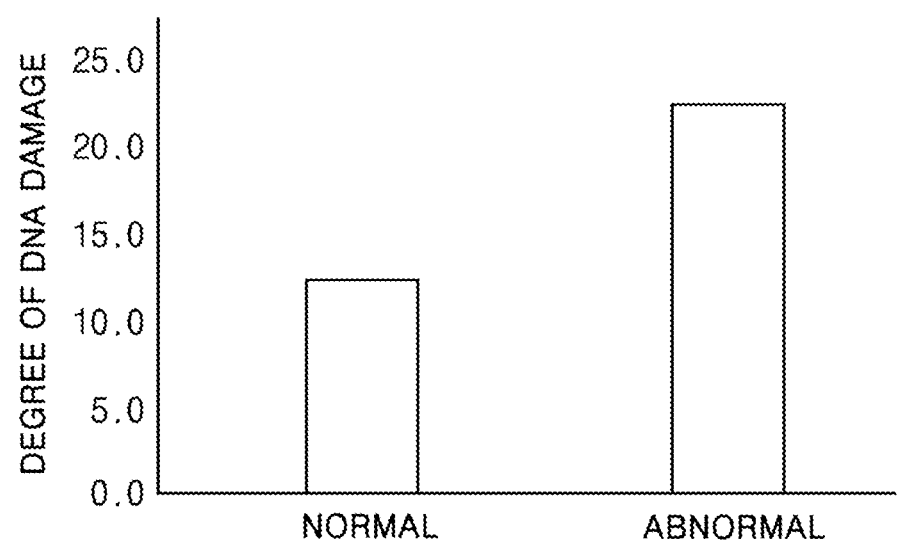
FIG. 10 is a diagram illustrating a degree of DNA damage (relative ratio) in the normal/abnormal samples using a Comet experiment method.
Figure 11A:
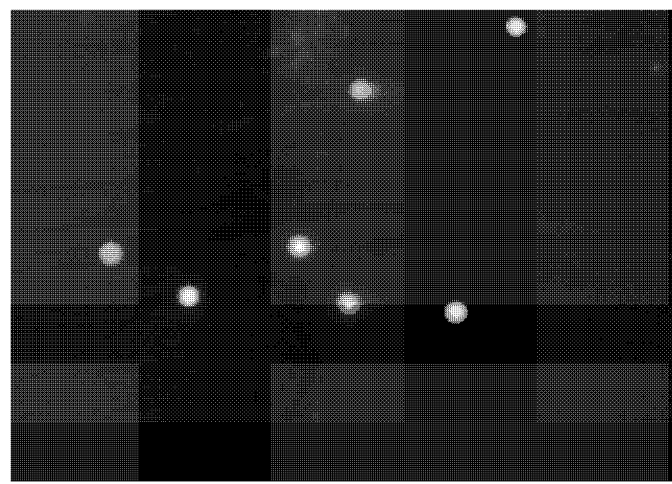
FIGS. 11A, 11B, 11C, and 11D are diagrams illustrating electrophoresis experiment results using the Comet experiment method. More specifically.
Figure 11B:
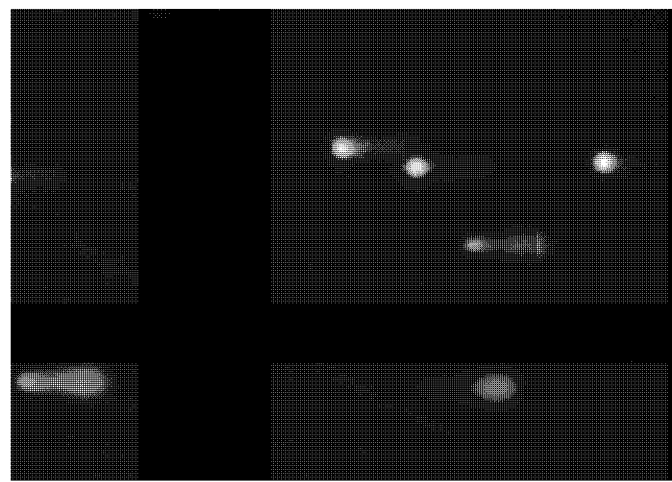
Figure 11C:
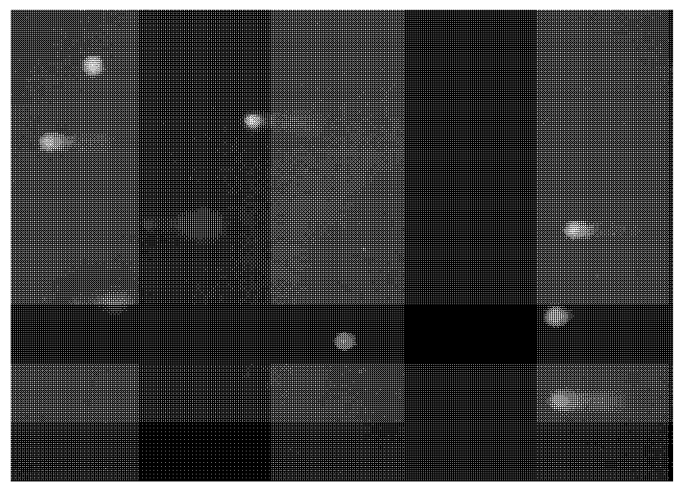
Figure 11D:
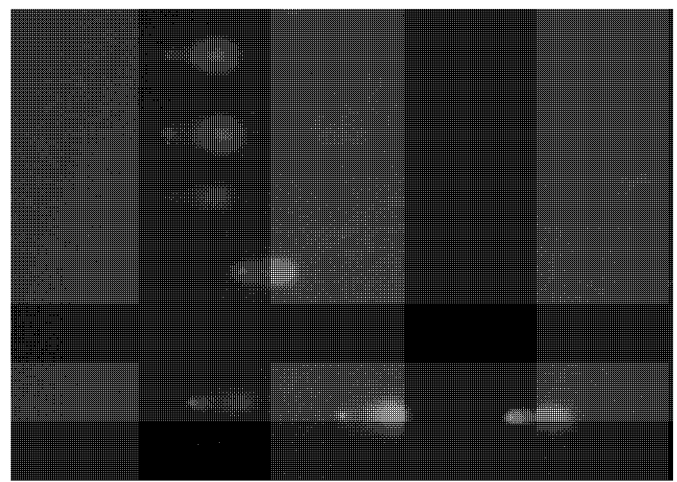

FIG. 10 illustrates the degree of DNA damage (relative ratio) in the normal/abnormal samples using the above-described Comet experiment method, and FIGS. 11A to 11D illustrate the electrophoresis experiment results using the Comet experiment method. In FIGS. 11A to 11D, FIG. 11A illustrates a case where no light is applied to the normal sample, FIG. 11B illustrates a case where light is applied to the normal sample, FIG. 11C illustrates a case where no light is applied to the abnormal sample, and FIG. 11D illustrates a case where light is applied to the abnormal sample.

Referring to FIG. 10, as a result of the Comet experiment, the abnormal sample showed a significantly higher degree of damage than the normal sample. These results are illustrated in FIGS. 11A to 11D, and it was confirmed that the length of the tail when light is applied to the abnormal sample was significantly longer than when light is applied to the normal sample.

In the exemplary embodiments of the present invention, it has been exemplarily described that cancer is diagnosed using blood as a sample, but other samples may be used as long as normal and abnormal cells have different degrees of damage by light. In addition to cancer, when the degree of damage to the normal and abnormal cells by light is different, it may be used for diagnosis of diseases other than cancer. In addition, although the Comet assay is used in the exemplary embodiment of the present invention, other assays may be used as long as the damage level of the normal and abnormal cells may be analyzed.

According to exemplary embodiments, a light irradiation apparatus is capable of simply and accurately diagnosing cancer by simply providing a sample containing a genetic material. Accordingly, it is possible to diagnose cancer in a short time and at a low cost.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light irradiation device comprising:
an injection unit configured to inject a sample; and
a light source configured to apply light to the sample to identify an abnormal cell in the sample, the light source including:
a substrate; and
a light emitter disposed on the substrate and comprising a light emitting diode,
wherein the light emitted from the light emitter is configured to cut a genetic material in the sample into sections of different sizes depending on a normal sample or an abnormal sample, and to deform the genetic material to different degrees, such that a determination of an abnormality of the sample is based on the degree of deformation of the genetic material, and wherein an irradiation amount or an irradiation intensity of the light emitted from the light emitter is configured to be provided at an intensity in which a cytotoxicity value of the sample is greater than or equal to a predetermined value, and in which a ratio of a degree of deformation of the genetic material of the normal sample to a degree of deformation of the genetic material of the abnormal sample is set to be a minimum value outside an error range.

2. The light irradiation device of claim 1, wherein the light emitted from the light emitter is in a wavelength band that generates reactive oxygen species, such that the light transmitted into the sample stimulates a photosensitive material in the sample.

3. The light irradiation device of claim 1, further comprising:
a reaction unit configured to inject a dyeing material into the sample to cause reaction between the dyeing material and the sample; and
an analysis unit configured to analyze the sample.

4. The light irradiation device of claim 3, further comprising a pre-processing unit configured to process the sample before providing the sample to the reaction unit.

5. The light irradiation device of claim 4, wherein the sample comprises blood.

6. The light irradiation device of claim 5, wherein the sample comprises leukocyte, and the pre-processing unit is configured to separate the leukocyte from whole blood.

7. The light irradiation device of claim 3, wherein the analysis unit is configured to be implemented in a Comet assay.

8. The light irradiation device of claim 7, wherein the analysis unit includes:
a data providing unit configured to provide a table quantifying a degree of damage of the genetic material according to a length of a tail in an electrophoresis result;
a comparison unit configured to compare lengths of tails of a normal cell and an abnormal cell with the length of the tail stored in the data providing unit; and
a determination unit configured to determine whether cancer occurs based on the comparison result of the comparison unit.

9. The light irradiation device of claim 8, wherein the data providing unit has a table corresponding to either a normal or an abnormal state according to the length of the tail.

10. The light irradiation device of claim 1, wherein the light emitted from the light emitter includes at least a portion of light in a blue wavelength band to an ultraviolet wavelength band.

11. The light irradiation device of claim 10, wherein the irradiation amount of the light is configured to be set within a limit in which cell viability of the normal sample is 75% or more.

12. The light irradiation device of claim 10, wherein the irradiation amount of the light is configured to be about 5 J/cm$^2$ or less, and the light is configured to be irradiated with an irradiation time of about 15 minutes or less.

13. The light irradiation device of claim 10, wherein the light is configured to be irradiated with a quantity of light of about 1.5 mW/cm$^2$ to about 100 mW/cm$^2$.

14. The light irradiation device of claim 1, wherein the light corresponds to at least one of light in UVA, UVB, and UVC wavelength bands and light in the blue wavelength band.

15. The light irradiation device of claim 1, wherein the light source includes at least two light emitters configured to emit light having different wavelengths.

16. A light irradiation device comprising:
an injection unit configured to inject a sample; and
a light source configured to apply light to the sample, wherein the light source includes:
- a light emitter configured to emit light to the sample to identify an abnormal cell in the sample; and
- a substrate on which the light emitter is disposed to dissipate heat generated from the light emitter, wherein the light emitted from the light emitter is configured to cut a DNA or RNA in the sample into sections of different sizes depending on a normal sample or an abnormal sample, and to deform the DNA or RNA to different degrees, such that a determination of the abnormality of the sample is based on the degree of deformation of the DNA or RNA, and wherein an irradiation amount or irradiation intensity of the light is configured to be set within a limit in which cell viability of the normal sample is 75% or more.

17. The light irradiation device of claim 16, wherein the light emitted from the light emitter includes at least a portion of light in a blue wavelength band to an ultraviolet wavelength band.

18. The light irradiation device of the claim 16, wherein the irradiation amount of the light is configured to be about 5 $J/cm^2$ or less, and the light is configured to be irradiated with an irradiation time of about 15 minutes or less.

19. The light irradiation device of claim 16, wherein the light is configured to be irradiated with a quantity of light of about 1.5 $mW/cm^2$ to about 100 $mW/cm^2$.

20. The light irradiation device of claim 16, wherein the sample comprises blood.

* * * * *